US010338265B2

(12) United States Patent
San Martin et al.

(10) Patent No.: US 10,338,265 B2
(45) Date of Patent: Jul. 2, 2019

(54) USING AN ARRAY OF SENSORS BETWEEN TWO TRANSMITTERS IN AN EDDY CURRENT LOGGING ENVIRONMENT

(71) Applicant: HALLIBURTON ENERGY SERVICES, INC., Houston, TX (US)

(72) Inventors: Luis Emilio San Martin, Houston, TX (US); Reza Khalaj Amineh, Houston, TX (US); Burkay Donderici, Houston, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 45 days.

(21) Appl. No.: 15/315,341

(22) PCT Filed: Jul. 13, 2015

(86) PCT No.: PCT/US2015/040194
§ 371 (c)(1),
(2) Date: Nov. 30, 2016

(87) PCT Pub. No.: WO2016/010917
PCT Pub. Date: Jan. 21, 2016

(65) Prior Publication Data
US 2017/0115426 A1    Apr. 27, 2017

Related U.S. Application Data

(60) Provisional application No. 62/023,875, filed on Jul. 12, 2014.

(51) Int. Cl.
*G01V 3/10* (2006.01)
*G01V 3/28* (2006.01)
(Continued)

(52) U.S. Cl.
CPC ............ *G01V 3/28* (2013.01); *E21B 47/00* (2013.01); *G01N 17/00* (2013.01); *G01N 27/902* (2013.01);
(Continued)

(58) Field of Classification Search
CPC ... G01V 3/28; G01V 3/38; G01V 3/18; G01V 3/20; G01V 3/22; G01V 3/24; G01V 3/26;
(Continued)

(56) References Cited

U.S. PATENT DOCUMENTS 4,292,589 A * 9/1981 Bonner ................ E21B 47/082
324/221
4,546,315 A * 10/1985 Minerbo ................ G01B 7/10
324/221
(Continued)

FOREIGN PATENT DOCUMENTS

| EP | 0370691 A1 | 5/1990 |
| JP | 2008-76180 | 4/2008 |
| WO | 2016/010917 | 1/2016 |

OTHER PUBLICATIONS

EP Application Serial No. 15821584.8, Extended European Search report, dated Nov. 20, 2017, 8 pgs.
(Continued)

*Primary Examiner* — Thang X Le
(74) *Attorney, Agent, or Firm* — Gilliam IP PLLC

(57) ABSTRACT

A magnetic imaging tool includes a body including at least two transmitters to transmit signals. The tool further includes an array of sensors coupled to the body to obtain eddy current responses to the signals from downhole tubulars. The array is located axially between two transmitters that produce magnetic fields with opposite orientations.

9 Claims, 4 Drawing Sheets

(51) Int. Cl.
*G01V 3/26* (2006.01)
*G01N 27/90* (2006.01)
*G01N 17/00* (2006.01)
*E21B 47/00* (2012.01)

(52) U.S. Cl.
CPC ....... *G01N 27/904* (2013.01); *G01N 27/9046* (2013.01); *G01V 3/26* (2013.01)

(58) Field of Classification Search
CPC . G01V 3/30; G01V 3/10; G01V 3/265; G01V 3/02; G01V 3/04; G01V 3/06; G01V 3/104; G01N 27/223; G01N 33/246; G01R 27/18; G01R 27/20; G01R 31/2621; G01R 31/2623; G01R 31/275; G01R 31/2884; G01R 31/2608; G01R 31/2614; G01R 31/2607; G01R 31/31924; G01R 31/3004; G01R 31/31922; G01R 31/318511; G01R 31/2831; G01R 31/318
See application file for complete search history.

(56) References Cited

U.S. PATENT DOCUMENTS

| | | | | |
|---|---|---|---|---|
| 5,670,878 | A * | 9/1997 | Katahara | G01N 27/82 324/221 |
| 5,914,595 | A | 6/1999 | Piriou et al. | |
| 7,420,367 | B2 | 9/2008 | Bespalov et al. | |
| 8,098,070 | B2 | 1/2012 | Lopez et al. | |
| 8,958,989 | B2 * | 2/2015 | Legendre | E21B 47/082 702/6 |
| 2007/0229066 | A1 | 10/2007 | Narishige et al. | |
| 2009/0195244 | A1 | 8/2009 | Mouget et al. | |
| 2009/0243618 | A1 | 10/2009 | Wang et al. | |
| 2013/0193953 | A1 * | 8/2013 | Yarbro | E21B 47/082 324/76.77 |
| 2016/0070018 | A1 * | 3/2016 | Nichols | E21B 47/00 324/339 |
| 2016/0160629 | A1 * | 6/2016 | Donderici | E21B 47/0006 324/238 |

OTHER PUBLICATIONS

Arbuzov, A. A. et al., "Memory Magnetic Imaging Defectoscopy," SPE 162054; Society of Petroleum Engineers, Russian Oil & Gas Exploration & Production Technical Conference and Exhibition held in Moscow, Russia, Oct. 16-18 2012, 10 pgs.

Garcia, Javier et al., "Successful Application of a New Electromagnetic Corrosion Tool for Well Integrity Evaluation in Old Wells Completed with Reduced Diameter Tubular," IPTC 16997, Prepared for presentation at the International Petroleum Technology Conference held in Beijing, China, Mar. 26-28, 2013, 12 pgs.

PCT International Search Report and Written Opinion, dated Oct. 26, 2015, Appl No. PCT/US2015/040194, "Using an Array of Sensors Between Two Transmitters in an Eddy Current Logging Environment," Filed Jul. 13, 2015, 13 pgs.

ID Application Serial No. P00201609149, Substantive Examination Report, dated Jan. 14, 2019, 3 pages.

MX Application Serial No. MX/a/2017/000036, Office Action, dated Oct. 4, 2018, 4 pages.

Monsegue, et al., "Scanning for Downhole Corrosion", Oilfield Review, Spring 2010, Issue 22 vol. 1, 9 pages.

* cited by examiner

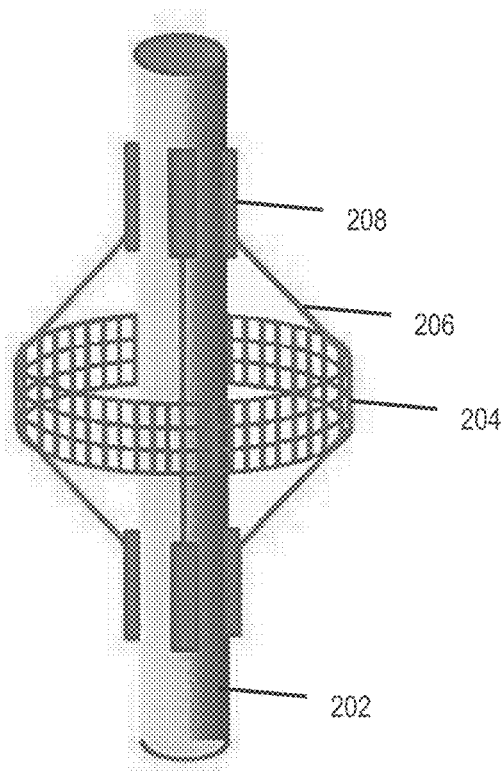
FIG. 2
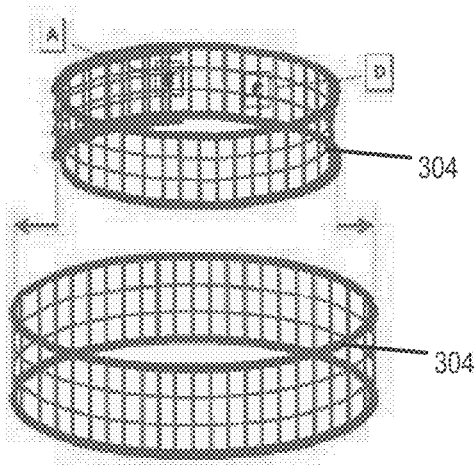
FIG. 3A
FIG. 3B
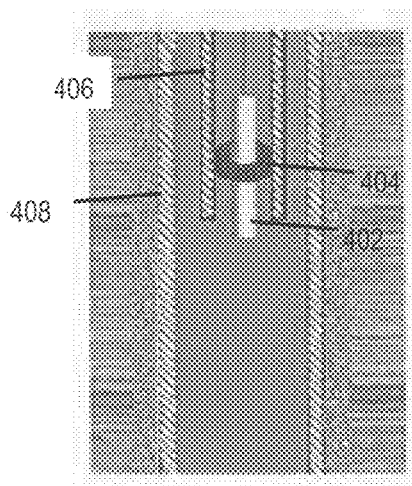
FIG. 4A
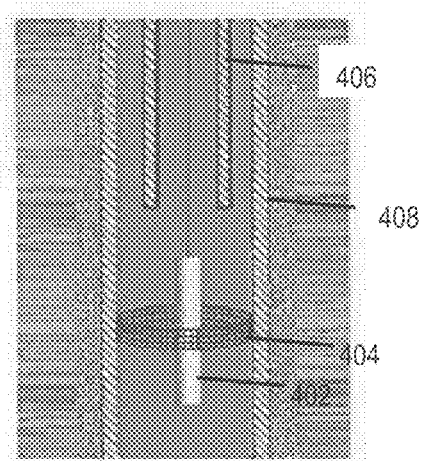
FIG. 4B

USING AN ARRAY OF SENSORS BETWEEN TWO TRANSMITTERS IN AN EDDY CURRENT LOGGING ENVIRONMENT

CROSS-REFERENCE TO RELATED APPLICATIONS

This application claims priority to U.S. Provisional Application Ser. No. 62/023,875 titled "Focused Magnetic Imaging Tool," filed Jul. 12, 2014 and incorporated herein by reference.

BACKGROUND

Scaling, corrosion, precipitates, and material defects are some problems faced by the oil and gas industry when managing production well and pipeline assets. These problems lead to diminished production in wells, casing integrity failure, and pipeline integrity failure any of which may result in costly and complex remediation measures. As such, electromagnetic techniques are commonly used to monitor the condition of the production and casing tubulars, collars, filters, packers, and perforations. These techniques can measure eddy current signal data to obtain accurate measurements of tubular thickness and tubular corrosion.

This form of corrosion monitoring can be especially useful to prevent tubular integrity failures in mature wells or non-producing wells. For example, corrosion damage typically decreases the thickness of a casing tubular. One electromagnetic technique used for defect detection is the eddy current technique. In this technique, when a transmitter coil emits a primary electromagnetic field, or signal, eddy currents are produced in the tubulars. The eddy currents produce secondary fields or signals. Next, the secondary signals, sometimes called eddy current responses, are received by the receiver coil. When recorded and processed, the data resulting from the secondary signals can be employed to perform an evaluation of the tubulars.

The diameter of an innermost tubular of concentric tubulars limits the size of the tool that can be deployed to monitor the integrity of all the concentric tubulars. Moreover, effectively monitoring the outermost tubulars from the innermost tubular is difficult because the tool must sense through a number of tubular layers. Finally, the electromagnetic field used in the eddy current technique is applied without regard to the specific tubular configuration encountered downhole.

BRIEF DESCRIPTION OF THE DRAWINGS

Accordingly, systems and methods for using an array of sensors between two transmitters in an eddy current logging environment are disclosed herein. In the following detailed description of the various disclosed embodiments, reference will be made to the accompanying drawings in which:

FIG. 2 is schematic view of an illustrative downhole tool;

FIGS. 3A-3B are sequence views of an illustrative array of sensors fully extending;

FIGS. 4A-4B are sequence views of an illustrative array of sensors fully extending in a downhole environment;

Figure 1:
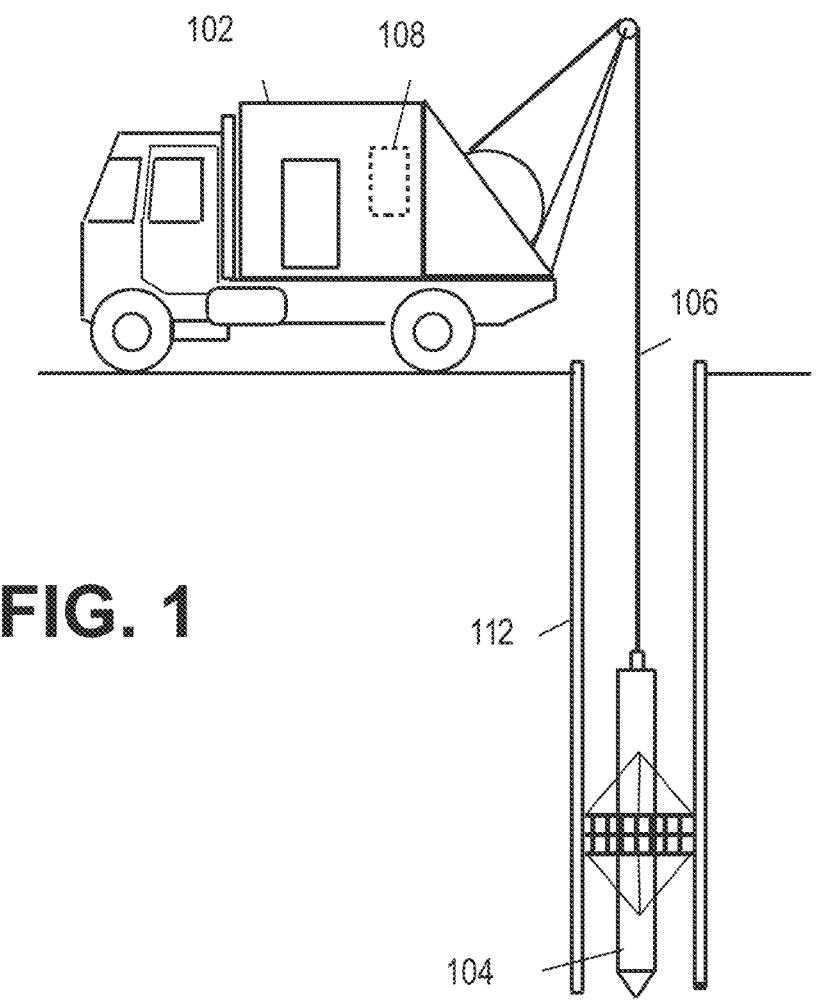
FIG. 1 is a contextual view of an illustrative wireline embodiment.

It should be understood, however, that the specific embodiments given in the drawings and detailed description thereto do not limit the disclosure. On the contrary, they provide the foundation for one of ordinary skill to discern the alternative forms, equivalents, and modifications that are encompassed together with one or more of the given embodiments in the scope of the appended claims.

Notation And Nomenclature

Certain terms are used throughout the following description and claims to refer to particular system components and configurations. As one of ordinary skill will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ". Also, the term "couple" or "couples" is intended to mean either an indirect or a direct electrical or physical connection. Thus, if a first device couples to a second device, that connection may be through a direct electrical connection, through an indirect electrical connection via other devices and connections, through a direct physical connection, or through an indirect physical connection via other devices and connections in various embodiments.

DETAILED DESCRIPTION

The issues identified in the background are at least partly addressed by systems and methods for using an array of sensors between two transmitters in an eddy current logging environment. Such a configuration leads to better inversion results, which leads to more accurate evaluation of downhole tubulars. In turn, decisions based on such results, such as estimating the useful life of downhole equipment or the cost versus benefit to repairing defects, are improved.

The disclosed systems and methods are best understood in terms of the context in which they are employed. As such, FIG. 1 shows a contextual view of an illustrative wireline embodiment. However, the disclosure is not limited to the context of FIG. 1. For example, the tool 104 may be employed in a slickline or coiled tubing embodiment using conductors and fiber optic cables for power and data transmissions. As another example, the tool 104 may be employed in an off-shore environment with appropriate supporting equipment as well. For example, the logging truck 104 may be replaced by off-shore equipment. Finally, the tool 104 may be used in a pipeline context as well. For example, instead of a wireline, a tractor may convey the tool 104 along a pipeline.

A logging truck 102 may suspend a wireline logging tool 104 on a wireline cable 106 having conductors for transporting power to the tool 104 and telemetry from the tool 104 to the surface. The tool 104 performs eddy current measurements in order to detect defects within the surrounding tubulars, and is described in detail with respect to FIG. 2. The tool 104 may include depth sensors, temperature sensors, pressure sensors, and the like that collect downhole measurements as a function of time. The collected measurements may provide context for interpreting and processing eddy current responses.

On the surface, a computer 108 may acquire and store measurement data from the tool 104 as a function of position along the borehole 112 and optionally as a function of azimuth. Though shown as an integrated part of the logging truck 102, the computer 108 may take different forms including a tablet computer, laptop computer, desktop computer, and virtual cloud computer accessible with a thin client. The computer 108 executes software to carry out necessary processing and enables a user to view and interact with a display of the resulting information, e.g., through a graphical user interface. For example, a log of tubular wall thicknesses or other indication of corrosion and defect locations may be displayed in pictorial or numerical form, enabling the user to initiate corrective actions if appropriate.

A processor coupled to memory may execute the software. The software may collect or obtain measurement data and organize it in a file or database. The software may also respond to user input via a keyboard or other input mechanism to display data as an image or movie on a monitor or other output mechanism such as a printer. In this way, a visual representation of the surrounding tubulars may be obtained, processed, and displayed. Furthermore, the software may issue an audio or visual alert to direct the user's attention to a particular location, result, or piece of data. The processor may perform any appropriate step described below. In at least one embodiment, the tool 104 itself may include a processor coupled with memory to obtain, store, and process measurement data taken by tool sensors, producing logs that are stored on a non-transient information storage medium. Such processing may occur downhole. With respect to FIG. 1, the use of the tool 104 is shown at one position. However, the tool 104 may operate at multiple positions as the tool 104 is conveyed along the borehole.

FIG. 2 is schematic view of an illustrative downhole tool 202 including movable arms 206, arm assemblies 208, and an array of sensors 204. The array of sensors 204 obtains eddy current responses, and may include a mesh of spatially distributed sensors that form a cylindrical shape. Each sensor on the mesh may measure a voltage induced in a solenoid of multiple windings by a magnetic field, and the use of multiple solenoids increases the number of measurements received at each location. The use of multiple windings in each solenoid enables the solenoids to be smaller so that the resolution of images based on measurements taken by the array of sensors 204 is improved compared to those based on conventional measurements. Each of the openings on the mesh represents the position of a unit set of sensors, and a unit set of sensors may measure the magnetic field in up to 3 orthogonal directions by using orthogonally distinct windings. For example, each unit set of sensors may include a square or rectangular wire to measure a magnetic field component extending perpendicular to the tool axis. Windings on the vertical portions of the wire may measure a magnetic field component extending parallel to the tool axis, and windings on the horizontal portions of the wire may measure a magnetic field component parallel to the face of the square or rectangle formed by the wire.

In at least one embodiment, flexible printed circuits are used to implement the mesh. For example, the flexible circuit may include a material that conforms to the shape of a surface that it contacts. By using such a flexible circuit, wiring may be greatly reduced due to inclusion of data transfer connections that terminate at the edges of the mesh. Accordingly, each sensor need not be coupled separately to a particular node. Multiple layers of circuits may be used to obtain higher sensor density.

The array of sensors 204 is coupled to movable arms 206. For example, a set of four movable arms 206 may be coupled to a top rail of the array of sensors 204 while another set of movable arms may be coupled to a bottom rail of the array of sensors 204. The movable arms 206 are coupled to the tool 202 body by arm assemblies 208. The arm assemblies 208 may be slidably coupled to the tool 202 body such that the cylinder formed by the array of sensors 204 may increase and decrease in diameter. FIG. 3A illustrates the array of sensors 304 in a semi-retracted state. In such a state, a portion of the array 304 overlaps another portion of the array 304. FIG. 3B illustrates the array of sensors 304 in a fully extended state. In such a state, no portion of the array 304 overlaps with another portion of the array 304. The degree of overlap may be monitored by tracking how far the arms are deployed.

Turning to FIG. 4A, the array 404 may be extended and retracted in response to changes in the nearest tubular diameter as the tool 402 moves downhole. For example, an inner tubular 406 may end at a certain borehole position, but an outer tubular 408 may continue further. Because the resolution of the measurements taken by the array 404 increases as the distance between the array 404 and tubular decreases, the arm assemblies, as shown in FIG. 2, may include spring mechanisms, actuators, motorized components, and the like to keep the array 404 at an operational distance from tubular at all times. The operational distance may include contact with a tubular or a constant radial distance from the tubular. As pictured, the operation distance includes contact with the inner tubular 406. As such, turning to FIG. 4B, the array 404 is extended to contact the outer tubular 408 once the tool 402 clears the inner tubular 406. Similarly, when the tool 402 is being pulled uphole, the array 404 may retract in response to the smaller diameter of the inner tubular 406. By making contact with the tubular, the array 404 may provide a centralizing effect for the tool 402.

Figure 5A:
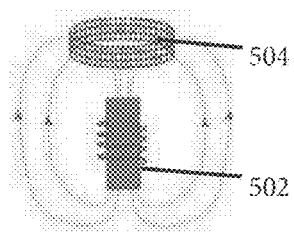
FIG. 5A-5E are schematic views of different configurations of illustrative arrays of sensors and transmitters.
Figure 5B:
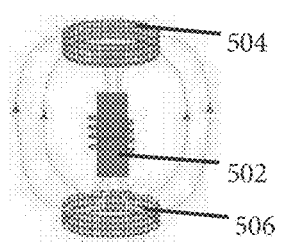
Figure 5C:
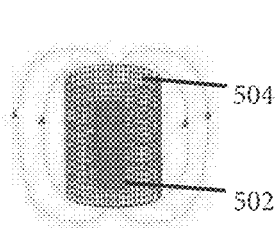

FIGS. 5A-5E are schematic views of different configurations of illustrative arrays 504, 506 and transmitters 502, 508 that are included the downhole tool described above. Each transmitter 502, 508 may include a core, and each core may be made of a magnetically-permeable material. The transmitters 502, 508 may include a winding, and the winding may be coupled to a power source that supplies and adjusts the current traveling through the winding. The array 504 may be positioned axially above the transmitter 502 as illustrated in FIG. 5A. The transmitter 502 may be positioned between two arrays 504, 506 as illustrated in FIG. 5B. The array 504 may surround the transmitter 502 at every axial depth as illustrated in FIG. 5C.

Figure 5D:
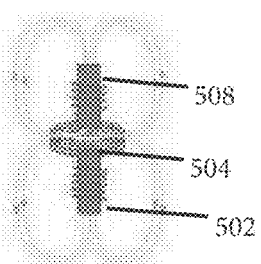
Figure 5E:
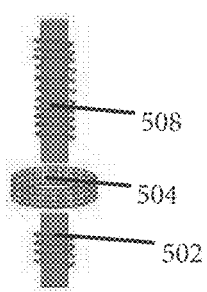

Turning to FIG. 5D, the array 504 may be positioned axially between two transmitters 502, 508 that produce magnetic fields with opposite orientations. For example, the power sources coupled to the two transmitters 502, 508 may operate in opposite phases, thereby resulting in magnetic fields of opposite orientations. As used herein, "opposite phase" refers to a phase difference equal to or, substantially equal to, 180 degrees. As another example, the winding about each core may be wound in opposite orientations or directions such that, opposing magnetic fields result when current is applied to the windings. The array 504 may provide feedback for adjusting the current in the windings in real time, i.e., during transmission. The current in the transmitters 502, 508 may be adjusted and optimized based on such feedback. For example, the currents may be optimally matched when the magnitude of the magnetic field component perpendicular to the tool axis is at its maximum at the axial middle of the array 504. One way to detect such a condition is to identify currents that produce a zero derivative between adjacent sensors at the center of the array 504, 506. Additionally, the array 504 may be positioned between two transmitters 502, 508 of different lengths as illustrated in FIG. 5E.

Figure 6:
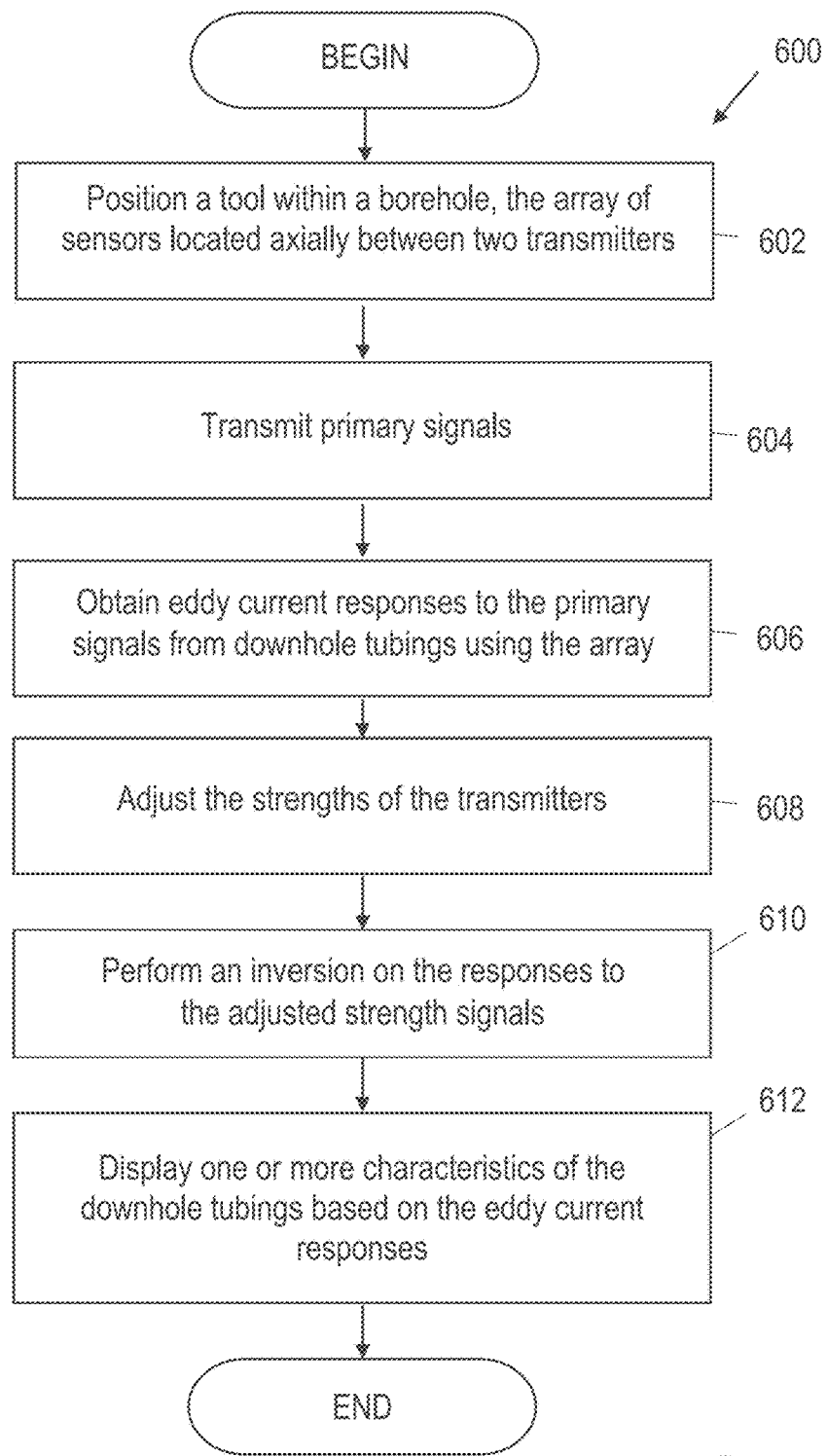
FIG. 6 is a flow diagram of an illustrative method of making downhole measurements using an array of sensors.

FIG. 6 illustrates a method 600 for making downhole measurements using an array of sensors described above. The method 600 is applicable in general inspection and evaluation contexts, and is also applicable in specific scenarios. For example, the array may measure the alignment of tubular openings in a flow control device. In this situation, it is necessary to verify the placement of the openings that control the flow of formation fluids to the surface. Some of the openings are located on an inner cylinder, and some of the openings are located on an outer cylinder. When the openings of the outer cylinder and inner cylinder are aligned, formation fluids flow into the borehole and from there to the surface. The array measures the openings with good resolution in both axial and azimuthal directions to verify proper alignment of the openings.

As another example, the method 600 is applicable when production tubular should not be pulled uphole. Specifically, the array may measure characteristics of production tubular and may measure characteristics of a casing tubular portion located at a greater depth than the production tubular (as illustrated in FIG. 4A) without the production tubular being pulled uphole. The array measures the casing tubular portion with good resolution despite being designed to fit within the production tubular.

Turning to the method, at 602, a tool is positioned at least partially within a borehole. The tool includes a body including at least two transmitters and an array of sensors coupled to the body. The array is located axially between two transmitters that produce magnetic fields. The magnetic fields of each of the transmitters may have similar or opposite polarities.

At 604, signals are transmitted using the transmitters. The signals may be primary signals used in the eddy current technique described above. The primary signals may produce eddy currents in tubulars surrounding the tool. The eddy currents produce secondary signals, or eddy current responses, which are obtained using the array at 606.

At 608, the strengths of the transmitters are adjusted. For example, substantially radial magnetic field components may be produced near the array of sensors, or substantially zero axial magnetic field components may be produced near the array of sensors in tubulars with no defect. The strength of the transmitters may be adjusted in real time, i.e., during transmission of the transmitting signals based on feedback from the array. The measurements between two sensors in the array may be compared, and the strength of the transmitters may be adjusted until the difference between measurements taken by adjacent sensors is zero or negligible. In such cases, the magnetic field may be perpendicular to the array.

At 610, an inversion is performed on the responses as measured by the array. An inversion is a mathematical process by which wall thickness, conduction, and other model parameters are iteratively modified to generate a model that is consistent with the data. An inversion may be performed on three orthogonal components of the responses simultaneously or on each of three orthogonal components of the responses separately. If the latter, the results of the separate inversions may subsequently be combined.

A location of a defect or opening may be identified in the tubulars based on the results of the inversion algorithm. Specifically, the inversion model specifies the wall thickness for each tubular such as production tubulars and casing tubulars. If the thickness is below a fixed or variable threshold at a particular location, in various embodiments, that location is identified as having a defect.

At 612, one or more characteristics of the downhole tubulars are displayed based on the eddy current responses. As described above, the location of the defect or opening may be displayed using appropriate hardware. Other characteristics that may be displayed include physical characteristics, such as the stand-off distances between the sensors and the tubulars and the thicknesses of the tubulars, as well as electrical characteristics of the tubulars, such as conductivity, permeability, and permittivity. Visualizations of the characteristics may be generated and used to identify features of the tubulars, such as cracks and corrosion. Notably, because of the improved resolution, the resulting images and visualizations indicate changes in tubular characteristics that correspond to very small features (on the order of 0.1 inches). Different colors, lines, and symbols may identify different characteristics on the display. For example, each tubular thickness may be plotted as separate curves. Alternatively, changes in the tubular thicknesses may be displayed as changes in the color. For example, a red hue may be used for losses, and a green hue may be used for gains.

A magnetic imaging tool includes a body including at least two transmitters to transmit signals. The tool further includes an array of sensors coupled to the body to obtain eddy current responses to the signals from downhole tubulars. The array is located axially between two transmitters that produce magnetic fields with opposite orientations.

The tool may further include a processor to generate an image of one or more of the downhole tubulars based on measurements from the array. A portion of the array may overlap with another portion of the array when the array is not fully extended. The array may measure corrosion in any of a plurality of concentric tubulars. The array may measure the alignment of tubular openings in a flow control device. The array may measure characteristics of production tubular and measures characteristics of a casing tubular portion located at a greater depth than the production tubular without the production tubular being pulled uphole. The tool may further include a processor to perform an inversion on the responses. The processor may perform the inversion on three orthogonal components of the responses simultaneously. The processor may perform the inversion on each of three orthogonal components of the responses separately and combine the results of the separate inversions.

A method for making downhole measurements includes positioning a tool at least partially within a borehole. The tool includes a body including at least two transmitters and an array of sensors coupled to the body. The array is located axially between two transmitters that produce magnetic fields. The method further includes transmitting signals using the transmitters and obtaining eddy current responses to the signals from downhole tubulars using the array. The method further includes displaying one or more characteristics of the downhole tubulars based on the eddy current responses.

The method may further include adjusting the strengths of the transmitters to produce substantially radial magnetic field components near the array of sensors, and two transmitters may have the same polarity. The method may further include adjusting the strengths of the transmitters to produce substantially zero magnetic field components near the array of sensors in tubulars with no defect, and the two transmitters may have opposite polarity. Adjusting the strengths may further include adjusting the strengths during transmission of the transmitting signals. The method may further include performing an inversion on the responses. Performing the inversion may include performing the inversion on three orthogonal components of the responses simultaneously.

Performing the inversion may include performing the inversion on each of three orthogonal components of the responses separately and combining the results of the separate inversions. The method may further include measuring corrosion in any of a plurality of concentric tubulars using the array. The method may further include measuring the alignment of tubular openings in a flow control device using the array. The method may further include measuring characteristics of production tubular using the array and measuring characteristics of a casing tubular portion located at a greater depth than the production tubular using the array without the production tubular being pulled uphole.

While the present disclosure has been described with respect to a limited number of embodiments, those skilled in the art will appreciate numerous modifications and variations therefrom. It is intended that the appended claims cover all such modifications and variations.

What is claimed is:

1. A magnetic imaging tool comprising:
a body comprising at least two transmitters to transmit signals; and
an array of sensors coupled to the body to obtain eddy current responses to the signals from downhole tubulars,
wherein the array of sensors is located axially between two transmitters that produce magnetic fields with opposite orientations and is extendable and retractable to obtain eddy current responses in different diameters of downhole tubulars.

2. The magnetic imaging tool of claim 1, further comprising a processor to generate an image of one or more of the downhole tubulars based on measurements from the array of sensors.

3. The magnetic imaging tool of claim 1, wherein a portion of the array of sensors overlaps with another portion of the array of sensors when the array of sensors is not fully extended.

4. The magnetic imaging tool of claim 1, wherein the array of sensors is to measure electromagnetic signals of a plurality of concentric tubulars from which a tubular thickness of at least one tubular is derived.

5. The magnetic imaging tool of claim 1, wherein the array of sensors is to measure the alignment of tubular openings in a flow control device.

6. The magnetic imaging tool of claim 1, wherein the array of sensors is to measure characteristics of a production tubular and to measure characteristics of a casing tubular portion located at a greater depth than the production tubular without the production tubular being pulled uphole.

7. The magnetic imaging tool of claim 1, further comprising a processor to perform an inversion on the eddy current responses.

8. The magnetic imaging tool of claim 7, wherein the processor is to perform the inversion on three orthogonal components of the eddy current responses simultaneously.

9. The magnetic imaging tool of claim 7, wherein the processor is to perform the inversion on each of three orthogonal components of the eddy current responses separately and to combine the results of the separate inversions.

* * * * *